United States Patent [19]

Widlund et al.

[11] 4,319,572
[45] Mar. 16, 1982

[54] DISPOSABLE DIAPER

[75] Inventors: Leif U. R. Widlund, Mölnlycke; Maj I. Ternström, Gothenburg, both of Sweden

[73] Assignee: Mölnlycke AB, Gothenburg, Sweden

[21] Appl. No.: 162,678

[22] Filed: Jun. 24, 1980

[30] Foreign Application Priority Data

Jul. 2, 1979 [SE] Sweden ................. 7905765

[51] Int. Cl.³ .............................. A61F 13/16
[52] U.S. Cl. .................... 128/284; 128/287; 128/290 R
[58] Field of Search ............. 128/287, 284, 290 R

[56] References Cited

U.S. PATENT DOCUMENTS

| Re. 26,151 | 1/1967 | Duncan et al. | 128/284 |
| 3,371,668 | 3/1968 | Johnson | 128/290 |
| 3,612,055 | 10/1971 | Mesek et al. | 128/287 |
| 3,616,114 | 10/1971 | Hamaguchi et al. | 428/352 |
| 3,646,937 | 3/1972 | Gellert | 128/287 |
| 3,860,003 | 1/1975 | Buell | 128/287 |
| 3,938,522 | 2/1976 | Repke | 128/287 |
| 4,041,951 | 8/1977 | Sanford | 128/287 |
| 4,050,462 | 9/1977 | Woon et al. | 128/287 |
| 4,074,716 | 2/1978 | Schaar | 128/287 |
| 4,081,301 | 3/1978 | Buell | 128/287 |
| 4,244,368 | 1/1981 | Caradonna | 128/287 |
| 4,253,461 | 3/1981 | Strickland et al. | 128/287 |

FOREIGN PATENT DOCUMENTS 955788 1/1950 France .
1350040 12/1963 France .

Primary Examiner—William J. Van Balen
Attorney, Agent, or Firm—Young & Thompson

[57] ABSTRACT

The invention relates to a disposable diaper, comprising a layer of a liquid-permeable, preferably non-woven material, intended to be placed in contact with the body of the user, and of a second layer of a liquid-impermeable material, between which layers an absorbent body is arranged, these two layers extending laterally outside the edges of the absorbent body. The special features of the diaper according to the invention are that the two layers beginning at the crotch portion extend laterally outside those side edges with a continuously increasing distance from the same towards the rear end of the diaper, thereby providing flaps with a gradually increasing width on both sides of the absorbent body, that at least one pretensioned elastic thread or the like is arranged in an essentially V-shaped pattern with the point of the pattern placed in the middle of the front end of the diaper and, that the portions of the thread running from the point extend from the middle of the front end of the diaper to the end of the crotch portion and continue along the edges of the flaps to the rear end of the diaper so that the flaps, when the diaper is in use will be in tight contact with the bottom of the user.

9 Claims, 6 Drawing Figures

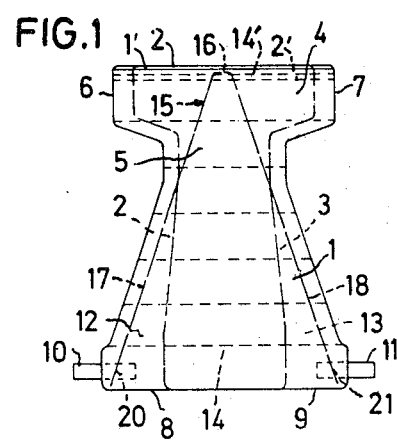
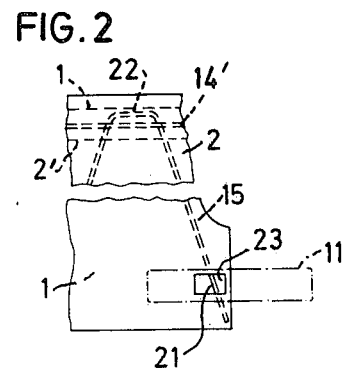
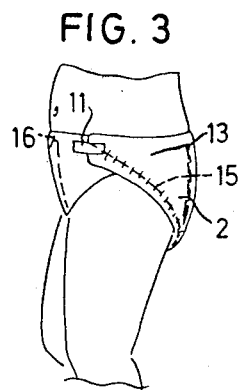
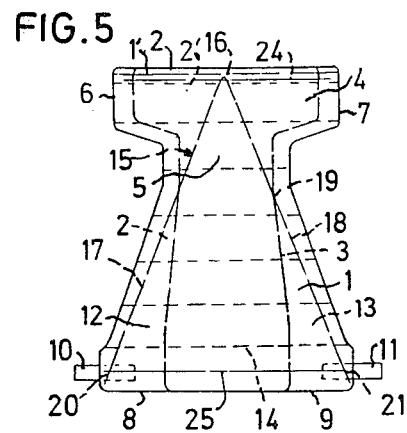
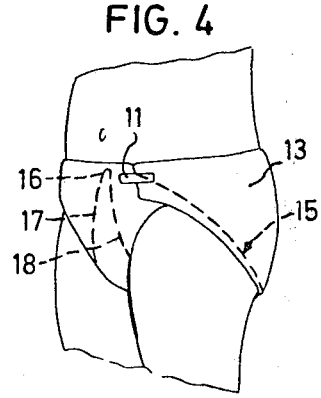
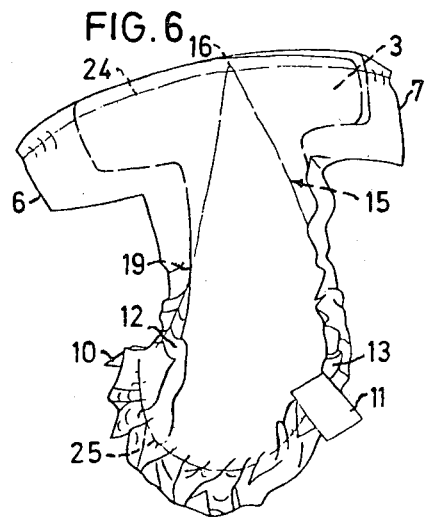

DISPOSABLE DIAPER

The present invention relates to disposable diapers. In recent years disposable diapers have virtually replaced cloth diapers intended for repeated use which are held in place on the user with the aid of plastic pants and which are washed after use for reuse.

Initially, disposable diapers consisted of a pad or folded fabric of an absorbent material and were held up with the aid of plastic or texile pants. Development led to the production of a so-called complete disposable diaper, consisting of a first outer layer of a liquid permeable material intended to lie in contact with the body of the user and of a second outer layer of a liquid impermeable material and of an absorbent body placed between said layers. The outer layers of these disposable diapers are extended outside the absorbent body to form attachment flaps which are intended to be applied around the waist of the user. These so-called complete disposable diapers are fastened on the user with the aid of strips of tape applied to said flaps One problem with complete disposable diapers is that the absorbent body has a certain stiffness making it difficult when applying the diaper with the aid of tape to make it close tightly around the user. Because of the stiffness of the absorbent body, it is impossible to avoid formation, especially after using the diaper for some time, of spaces between the diaper and the waist of the child and/or between the diaper and the legs of the child with subsequent risk of leakage. Attempts to eliminate the risk of leakage have involved supplementing so-called complete disposable diapers with elastic bands or the like intended to make the diaper close tightly around the user.

There are different types of disposable diapers on the market, which are provided with elastic bands extending along the sides. Common to these previously known types of disposable diapers with elastic bands is that the bands are applied primarily to prevent leakage of urine.

U.S. Pat. No. 3,860,003 describes a diaper which is provided in its crotch portion with a flexible side flap which extends out from and along each side edge of the absorbent body. The absorbent body is significantly narrower in the crotch area than in the rest of the diaper and an elastic band is attached to the side flap spced from the side edge of the absorbent body at least 19 mm. Thus, elastic side flaps are formed which close tightly around the legs of the child when using the diaper.

The arrangement of the elastic flaps appears to reduce the risk of urine leakage, but it still has a number of disadvantages. Leakage from the absorbent core is collected inside the elastic flaps and can give rise to skin irritation. Furthermore the width of the absorbent body must be reduced substantially in the crotch area to provide sufficient width to the elastic flaps. This means that the absorbent material when the diapers are used will become very wet quickly and leakage of urine will occur in spite of the sealing elastic bands. Furthermore the drastically reduced width of the absorbent body in the crotch area results in disintegration in said area because of the large amount of liquid, thereby preventing liquid transfer to the unused portions of the absorbent body.

The above mentioned disadvantages of the diaper according to U.S. Pat. No. 3,860,003 are described in detail in U.S. Pat. No. 4,050,462 according to which, in order to avoid said disadvantages, another construction of the diaper is chosen. The elastic bands in the diaper according to the last-mentioned publication are applied in the crotch area of the diaper as close to the absorbent body as is practically possible. The elastic bands thereby achieve a pulling together of the absorbent body in the crotch area so that the thickness of the absorbent body increases in this area. The combination of the increased absorbent capacity per unit of area in the crotch area and the sealing of the elastic bands around the users legs, according to U.S. Pat. No. 4,050,462, virtually eliminates the risk of urine leakage. The last-mentioned publication maintains that the uneven areas formed in the crotch area of the absorbent body serve as cushions and serve to prevent the elastic bands chafing and making marks on the skin of the user. Even if, contrary to expectations, these cushions were to reduce the tendency of the elastic bands to chafe the skin to some degree, it is unavoidable that the arrangement of elastic bands in the crotch area to one side of the absorbent body will produce significant chafing against the legs of the child. When the child moves either by crawling or walking, the leg movements result in a significant increase in the tension in the elastic band which can thereby cause chafing marks around the legs of the child.

It is evident from the above, that in spite of the great efforts up to now, no one has been successful in producing a disposable diaper equipped with elastic bands, which functions satisfactorily in all respects.

In previously known diapers with elastic bands, cords etc., the bands have not been applied so that they follow the body of the user in a natural manner. Rather, as was mentioned above, two elastic bands or the like have been applied so as to extend essentially parallel with each other over the diaper.

The present invention relates to a disposable diaper with an absorbent body which is placed inside a casing made with a crotch portion, said casing comprising a first layer of a liquid-permeable material intended to lie in contact with the user's body, and a second layer of a liquid-impermeable material, an absorbent body being disposed between said two layers which extend, at least laterally, outside the edges of the absorbent body.

The purpose of the present invention is to improve the complete disposable diaper described in the introduction so that its fit is improved, i.e. so that the diaper closes tightly all around against the body of the user, which results in increased security against leakage.

Another purpose of the present invention is to apply an elastic thread or the like, the extension of which over the diaper is adapted to the user's body.

According to the invention this is achieved by the layers in the direction towards the rear end of the diaper, and beginning with the crotch portion, extending laterally outside said edges with a continuously increasing distance from the same, thereby forming flaps with gradually increasing width on both sides of the absorbent body, with at least one pretensioned elastic means applied in an essentially V-shaped pattern with the point of the pattern placed in the centre of the front end of the diaper, and with the portions of this pattern running from the point extending from the centre of the front diaper end to the end of the crotch portion and on along the edges of the flaps to the rear end of the diaper so that the flaps, when the diaper is used, will lie tightly against the bottom of the user.

Suitably the elastic means is applied between the two outer layers and on one side surface of the absorbing body within the area in which the means extends over the absorbent body, the means being securely fixed to at least one of the layers and at least to the front and rear ends of the diaper.

The diaper according to the invention is preferably provided with strips of tape for fastening on the diaper, fixed to the liquid-impermeable layer at the free corner portions of the flaps. According to one embodiment, the end portions of the elastic means at the rear end of the diaper are located under the strips of tape joined to the flaps, and the liquid-impermeable layer has holes at the attachment locations for the tape, in which said end portions of the means are arranged and thereby anchored to the strips of tape. In addition to securely anchoring the end portions of the elastic means, this arrangement also transfers the tension in the means directly to the tape which is favourable for the tightening of the diaper.

Suitably the elastic means, at least at the front and rear ends of the diaper, is fixed to at least one of the layers by means of an adhesive, for example a thermoplastic adhesive.

According to a suitable embodiment, the elastic means extends through a bead of adhesive, which joins the front end portions of the two casing layers, and the elastic means has a portion at said bead.

It has proved to be especially advantageous to use elastic means in the form of covered elastic threads. These are easier to fix with adhesive than rubber bands for example and result in significantly less chafing against the skin of the user.

For the purpose of improving the tension against the waist the elastic means is joined, at least at one end of the diaper, with an additional pretensioned elastic means running transverse to the diaper.

To improve security against urine leakage the absorbent body is made in its portions in the crotch and between the two extending ends of the elastic means with a greater thickness than the rest of the body.

The invention will be described in more detail below with reference to an embodiment which is shown in the accompanying drawing, of which FIG. 1 shows a plan view of a diaper according to the invention extended, FIG. 2 shows on a larger scale and in a broken view portions of the front and rear ends of the diaper to illustrate the anchoring of the elastic thread, FIGS. 3 and 4 show two perspective views of the diaper in place on a child, FIG. 5 shows a somewhat modified embodiment of the diaper according to the invention and FIG. 6 shows on a larger scale the diaper according to FIG. 5 when it is not stretched out.

The disposable diaper according to the invention consists of a first outer layer 1 of a liquid-permeable, preferably non-woven textile which when used is intended to be applied against the body of the user, and of a second outer layer 2 of a liquid-impermeable material, for example polyethylene, and of an absorbent body 3 disposed between the two outer layers.

The absorbent body has a cross portion 4 at one end, which, as will be seen from FIG. 1 extends the width of this end and is designed, when the diaper is used, to be placed in front of the legs of the child. Furthermore the absorbent body is made thicker in one area 5 at the crotch of the diaper, i.e. essentially behind the cross portion 4. The diaper has the greatest absorption capacity where the need is greatest and so the risk of urine leakage is quite small. The outer layers 1,2 which extend laterally outside the absorbent body, are formed at both ends into attachment flaps 6,7 and 8,9 respectively which are intended to be applied around the waist of the user. Tape strips 10,11 are fixed to the rear flaps 8,9 of the diaper for joining the flaps at the front and rear ends of the diaper when putting on the diaper. Beginning at a portion just below the crotch portion of the diaper, the two outer layers extend with continuously increasing lateral extension from the side edges of the absorbent body so that essentially triangular flaps 12,13 are formed on both sides of the absorbent body.

The two outer layers are joined together along their edge portions and are also joined by means of lateral adhesive line 14 with each other and with the absorbent body 3.

An elastic thread 15 or the like is arranged in an essentially V-shaped pattern across the entire diaper. The point 16 of the V-shaped pattern is located in a centre of the front end of the diaper, from which thread portions 17, 18 extend along essentially straight lines to the rear end of the diaper across the absorbent body 3 to a location 19 below the crotch portion of the diaper and from there along the outer edge portion of the respective triangular flap. The elastic thread 15 is disposed between the two outer layers and is securely joined to them at the point of the thread pattern and at the two thread end portions 20,21. The elastic thread is also joined at separate locations along its length with the outer layers or the absorbent body 3 by means of the transverse line of the adhesive. In the embodiment shown, the liquid-impermeable outer layer 2 is folded over the front edge portion of the diaper and the elastic thread 15 extends at its V-shaped point through the adhesive line 14', which joins the front end portions of the two outer layers and has a thread portion 22 in front of said adhesive line, as is most clearly shown in FIG. 2. The edges of the two outer layers at the front end of the diaper are labeled 1' and 2' in the drawing.

The anchoring of the thread end portions 20, 21 at the rear end of the diaper is shown in FIG. 2. The thread end portions are located in the middle of the tape strip portions joined to the flaps and in the liquid-impermeable outer layer 2 a hole 23 is arranged right over said thread end portions. Said thread end portions are thereby anchored by the strips of tape.

The elastic thread 15 is arranged pretensioned and when the diaper is in place on the child the thread holds the triangular flaps 12,13 tightly against the child's bottom. By virtue of the fact that the thread is arranged in the manner shown in FIG. 1 in an essentially V-shaped pattern, the thread end portions 20, 21 after putting the diaper on a child, will essentially extend up to a location at the V-shaped point. FIGS. 3 and 4 show how the elastic thread after application of the diaper follows the body of the child. By virtue of the special arrangement of the elastic thread, there are no undesirable tensions occurring when the child moves which could cause chafing marks on the skin. The thread will thus hold the triangular flaps against the bottom of the child and provide effective sealing against excrement leakage at the same time as the diaper is comfortable to the wearer, i.e. does not chafe.

The risk of chafing against the skin has been minimized by virtue of the fact that the elastic thread does not go outside the absorbent body 3 except behind the crotch. Since the point of the thread pattern is placed in the centre of the front edge of the diaper, the front edges are drawn down and together somewhat in the centre, producing an elastic effect in the waist which in turn provides a better fit around the waist and less leakage at the stomach and back. The elastic effect in the waist can be varied both by varying the thread tension and by varying the distance between the two points of attachment to which the thread is attached at the line of adhesive 14'.

Since the thread portions 17, 18 extend around the bottom of the user and essentially all the way to a location at the point of the thread pattern, these thread portions will contribute to the tensioning of the diaper around the waist of the user.

The elastic means in the diaper according to the invention consist of covered elastic thread, in which the elastic thread can, for example, be Elastan®.

The covering can be achieved by an essentially non-elastic thread, for example cotton, being wrapped doubly around the elastic thread.

Another suitable embodiment of covered elastic thread is achieved by the elastic thread being woven into a non-elastic textile thread.

Covered elastic thread can be achieved by a so called "guipmaille process", where a mesh of textile thread is knitted around the elastic thread. The advantage of the last mentioned embodiment is that the elastic thread remains in the mesh even if the thread breaks.

The use of covered elastic thread as an elastic means, instead of elastic means in the form of rubber bands used in complete disposable diapes up to now has several essential advantages.

When using a rubber band, the tension of the band increases sharply as the band is stretched resulting in chafing against the skin of the user.

The elastic thread used in the diaper according to the invention has, on the other hand, essentially the same thread tension even if the thread is stretched.

The covering of the elastic thread facilitates the glueing on of the thread since the adhesive is absorbed better than what would be the case with a bare thread.

It should be pointed out here, that it is difficult to glue rubber bands since they have a smooth surface. When arranging a rubber band on disposable diapers, the band must be glued along its entire length for satisfactory holding, thus sacrificing a large portion of the elastic effect of the band.

When using covered elastic thread, it is sufficient to attach it at separate places along the length, for example only at the front end with ends of the diaper. The elasticity of the elastic thread can thereby be fully exploited.

In the embodiment shown in FIGS. 5 and 6 of the diaper according to the invention the portions corresponding to similar portions in the diaper according to FIGS. 1 and 2 have been provided with the same reference numerals.

The diaper shown in FIGS. 5 and 6 differs from the previously described embodiment in that the diaper has been supplemented with transverse elastic means 24 and 25 at the front and rear ends of the diaper.

The elastic means 24 and 25 are intended to serve as a waist elastic for tensioning the diaper around the waist of the user.

As is evident from FIGS. 5 and 6, the front elastic means 24 runs through the point of the V-shaped elastic means 15, i.e. a portion of the means 15 runs around the thread 24. Thus, the elastic in threads 15 and 24 will cooperate.

The end portions of the elastic means 25 are attached essentially at the same location and in the same manner as the thread end portions 20, 21, the anchoring of which was described with reference to FIG. 2.

The invention is not limited to the embodiments described above. Rather, a number of modifications are possible within the scope of the following claims.

The adsorbent body need not, of course, be T-shaped, but can have any suitable form, for example essentially rectangular. Instead of providing the diaper with elastic transverse means both at the front and rear ends of the diaper, the diaper can be provided with only one transverse elastic means 24 or 25 at the front or rear end of the diaper. The elastic means 15, 24 and 25 in the embodiments shown have been simple covered elastic threads, but it is of course possible that the elastic means 15,24 or 25 consist of two or more essentially parallel covered elastic threads.

The thread end portions of the elastic means 15 and 25 need not be anchored as described with reference to FIG. 2. They can, of course, be attached in another suitable manner, for example with adhesive.

What we claim is:

1. In a disposable diaper with an adsorbent body, which is placed inside a casing made with a crotch portion, said casing comprising a first layer of a liquid-permeable material, intended to lie in contact with the body of the user and a second layer of a liquid-impermeable material, between which two layers the absorbent body is arranged and which extend at least laterally outside the edges of the absorbent body; the improvement in which the layers, in a direction towards the rear end of the diaper and beginning at the crotch portion, extend laterally outside said edges with a continuously increasing distance from the same, thereby forming flaps with gradually increasing width on both sides of the absorbent body, and at least one pretensioned elastic means arranged in an essentially V-shaped pattern with the point of the pattern placed in the middle of the front end of the diaper, the portions of this pattern running from the point extending from the middle of the front diaper end to the end of the crotch portion and continuing along the edges of the flaps to the rear end of the diaper so that when the diaper is used the flaps will be in tight contact against the bottom of the user.

2. Diaper according to claim 1, in which the elastic means is arranged between the two outer layers and on one side surface of the absorbent body, the means being securely fixed to at least one of the other layers and at least to the front and rear ends of the diaper.

3. Diaper according to claim 1 and with strips of tape for holding the diaper in place, arranged on the liquid impermeable layer at the free corner portions of the flaps, in which the end portions of the elastic means at the rear end of the diaper are disposed in the middle of the strips of tape joined to the flaps and the liquid-impremeable layer at the points of attachment for the tape has holes in which said end portions of the means are arranged and are thereby anchored to the strips of tape.

4. Diaper according to claim 2, in which the elastic means, at least at the front and rear ends of the diaper, is attached to at least one of the layers by means of an adhesive, for example thermoplastic adhesive.

5. Diaper according to claim 1, in which the elastic means, at the point of the pattern, extends through a line of adhesive which joins the front end portions of the two casing layers and has a portion in front of said line.

6. Diaper according to claim 1, in which the elastic means, at least at one end of the diaper, is joined to an additional pre-tensioned, elastic means running transverse to the diaper.

7. Diaper according to claim 1, in which the elastic means consists of covered elastic threads.

8. Diaper according to claim 1, in which the portion of the absorbent body located at the crotch portion and between the extending portions of the elastic means has a greater thickness than the rest of the body.

9. Diaper according to claim 3, in which the elastic means, at least at the front and rear ends of the diaper, is attached to at least one of the layers by means of an adhesive, for example thermoplastic adhesive.

* * * * *